United States Patent
Cai et al.

(10) Patent No.: US 7,407,977 B2
(45) Date of Patent: Aug. 5, 2008

(54) SUBSTITUTED N-ACYL-2-AMINOTHIAZOLES

(75) Inventors: Jianping Cai, West Caldwell, NJ (US); Adrian Wai-Hing, Glen Rock, NJ (US); Fariborz Firooznia, Florham Park, NJ (US); Kevin Richard Guertin, Verona, NJ (US); Lida Qi, Leonia, NJ (US)

(73) Assignee: Hoffman-La Roche Inc., Nutley, NJ (US)

( * ) Notice: Subject to any disclaimer, the term of this patent is extended or adjusted under 35 U.S.C. 154(b) by 473 days.

(21) Appl. No.: 11/193,766

(22) Filed: Jul. 29, 2005

(65) Prior Publication Data
US 2006/0030589 A1 Feb. 9, 2006

Related U.S. Application Data

(60) Provisional application No. 60/599,167, filed on Aug. 5, 2004, provisional application No. 60/689,170, filed on Jun. 10, 2005.

(51) Int. Cl.
*A61K 31/428* (2006.01)
*C07D 277/60* (2006.01)
*C07D 513/00* (2006.01)

(52) U.S. Cl. .................. 514/366; 548/146; 548/148; 548/150; 548/300.1; 548/311.1; 548/311.7; 548/356.1; 548/364.1; 548/364.4; 546/184; 546/268.1; 514/365

(58) Field of Classification Search .......... 548/146, 548/148, 150, 300.1, 311.1, 311.7, 356.1, 548/364.1, 364.4; 546/184, 268.1; 514/365, 514/366
See application file for complete search history.

(56) References Cited

U.S. PATENT DOCUMENTS

| | | | |
|---|---|---|---|
| 4,877,876 A | 10/1989 | Tsuji et al. | |
| 4,929,623 A | 5/1990 | Abe et al. | |
| 5,189,049 A | 2/1993 | Frehel et al. | |
| 5,480,874 A * | 1/1996 | Shoji et al. | ........ 514/80 |
| 6,476,059 B1 | 11/2002 | Jahne et al. | |
| 7,026,334 B1 * | 4/2006 | Takemoto et al. | ...... 514/314 |

FOREIGN PATENT DOCUMENTS

| | | |
|---|---|---|
| GB | 1 296 561 | 1/1969 |
| JP | 45-38614 | 12/1970 |
| JP | 45-38615 | 12/1970 |
| JP | 60205454 | 10/1985 |
| JP | 2004 18489 | 1/2004 |

OTHER PUBLICATIONS

Chordia et al, "2-Aminothiazoles: A New Class of Agonist Allosteric Enhancers of $A_1$ Adenosine Receptors" Bioorganic & Medicinal Chemistry Letters, vol. 12 pp. 1563-1566 (2002).
Van Tilburg et al, "Substituted 4-Phenyl-2-(phenylcarboxamido)-1,3-thiazole Derivatives as Antagonists for the Adenosine A1 Receptor", Bioorganic & Medicinal Chemistry Letters, vol. 11, pp. 2017-2019 (2001).
Ohkubo et al, Studies on Cerebral Protective Agents, VIII [1a], Synthesis of 2-Aminothiazoles and 2-Thiazolecarboxamides with Antianoxic Activity, Chem. and Pharam. Bulletin, vol. 43, No. 9 pp. 1497-1504 (1995).
Database Chemcats—XP-002356245 (2005).
Database Chemcats, XP-002356246 (2005).
Database Registry, XP-002356247 (2004).
King et al, "The Reaction of Ketones with Iodine and Thiourea" Jour. of the Amer. Chem. Soc., vol. 72, pp. 3722-3725 (1950).
Zhurnal Obshchei Khimii, vol. 20, pp. 1658-1661.
Database Registry—XP-002352857 (2003).
Database Chemcats—XP-002356248 (2003).
Mehra, S.C. et al, Journ. of Chem. and Eng. Data, vol. 23, No. 1 (1978) pp. 89-90 (XP009056640).
Pentimalli, L, "Coloranti tiazolici a sviluppo e a dispersione Azoici da acetacetamido-tiazoli", Bollettino Scientifco della Facolta di Chimica Industriale di Bologna, vol. 23, No. 1 (1965) p. 7-14 (XP 009056637).
Database Chemcats, XP-002356249 (2003).
Database Registry XP-00356250 (2002).
Database Chemcats XP-002356251 (2005).
Database Registry XP-002356252 (2004).
Yamane, F., Nippon Kagaku Zasshi, vol. 90 (1969), pp. 569-571 (XP-009056348).
Pandeya et al., Indian Drugs, 23, pp. 146-151 (1985).
Neela et al., Synthetic Communications, 23, pp. 2347-2353 (1993).
Göblyös et al., Bioorganic & Medicinal Chemistry, 13, pp. 2079-2087 (2005).

* cited by examiner

*Primary Examiner*—Golam M Shameem
(74) *Attorney, Agent, or Firm*—George W. Johnston; Patricia S. Rocha-Tramaloni

(57) ABSTRACT

There are presented compounds of the formula

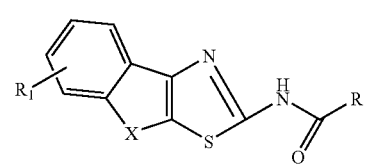

or a pharmaceutically acceptable salt thereof, which are useful in the treatment of diabetes, diabetic retinopathy, asthma and diarrhea.

9 Claims, No Drawings

SUBSTITUTED N-ACYL-2-AMINOTHIAZOLES

PRIORITY TO RELATED APPLICATIONS

This application claims the benefit of Provisional Application(s) Ser. Nos. 60/599,167, filed Aug. 5, 2004 and 60/689,170, filed Jun. 10, 2005.

FIELD OF THE INVENTION

This invention relates to at least one compound of the formula I

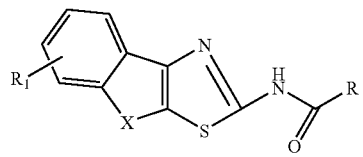

or pharmaceutically acceptable salts thereof, wherein X, R and $R_1$ are described in this application. These compounds are believed to act primarily as Adenosine 2B Receptor Antagonists and therefore to have potential for the treatment of diabetes, diabetic retinopathy, asthma and diarrhea.

BACKGROUND OF THE INVENTION

Adenosine is an autocoid produced in many tissues to mediate various functions through four receptor subtypes, A1, A2A, A2B and A3. All four receptors belong to the class of G-protein coupled receptors (GPCRs), which contain seven helical hydrophobic domains that span plasma membrane, connected by hydrophilic extracellular and intracellular loops. A1 and A3 receptors couple to Gi and Go proteins, while A2A and A2B receptors are coupled to Gs proteins. Because of these differences, adenosine signals an increase in intracellular cAMP levels via its action through A2A and A2B receptors, and a decrease through A1 and A3 receptors. In addition, adenosine increases intracellular calcium ion levels via A2B receptor, because of its coupling to Gq proteins.

The compounds of formula I have potent adenosine human A2B receptor antagonist activity as measured in CHO-A2B-cAMP assay. These compounds also have residual potent human A1 and human A2A antagonist activity, as measured in the radiolabeled ligand binding assays.

The study of role of A2B receptor's functional activity on various cell types was complicated by the absence of selective A2B agonists and antagonists vs other three receptors. Typically, the functional activity of A2B receptor is deduced by the absence of effects of the selective agonists and antagonists at other three adenosine receptors, while eliciting response with NECA, a potent and non-selective adenosine receptor agonist. Usually, the role of A2B receptor on a given cell type, is identified when the following unique order of agonist potency is observed; NECA (non-selective)>PIA (A1-selective agonist)>IB-MECA (A3-selective agonist)>CGS-21680 (A2A-selective agonist).

Adenosine's relative agonist potency against the four receptors was determined to be, A1 ($EC_{50}$–0.31 uM)>A3 ($EC_{50}$–0.29 uM)>A2A ($EC_{50}$–0.7)>A2B ($EC_{50}$ –24 uM), suggesting a unique role for A2B receptor during chronic, high oxidative stress conditions, including but not limited to hyperglycemia, mast-cell activation, and gastrointestinal tract inflammation. In spite of low agonist potency of adenosine to the A2B receptor, numerous compounds with high A2B receptor antagonist potency have been reported.

Using specific agonists and antagonists, Eisai researchers demonstrated the key role of A2B receptor antagonism in inhibiting hepatic glucose production, and a potent A2B receptor antagonist and an inhibitor of glucose production in rat primary hepatocytes was also shown to lower fasting and fed glucose levels in KK-Ay mice, a well recognized model of type 2 diabetes. Thus, compounds of present invention have utility in preventing and/or treating type 2 diabetes.

A2B receptors are also present in the plasma membranes of endothelial cells and have been found to stimulate their growth. Since this will lead to growth of new blood vessels (angiogenesis). An object of this invention is to prevent and/or treat diseases characterized by abnormal blood vessel growth, such as diabetic retinopathy.

Using immuno-fluorescence techniques with a specific anti-human A2B-antibody indicated the presence of A2B receptors in human lung mast cells obtained from asthmatics by bronchoalveolar lavage cells. Thus, the compound of formula I provide a method of preventing and/or treating asthma, bronchospastic and allergic diseases as well as other obstructive airway-type diseases.

A2B receptors are found in the colon in the basolateral domains of intestinal epithelial cells, and increases chloride ion secretion in reaction to the gastrointestinal tract inflammation in diseases such as, diarrhea. Thus, the compounds of formula I provide a method to treat inflammatory gastrointestinal tract disorders including diarrhea.

The compounds of present invention also have potent antagonist activity against A1 and A2A receptors, in addition to the A2B receptors. Hence, compounds of formula I provide methods to treat diseases where adenosine A1, A2A and A2B receptor antagonism plays a role, such as depression, Parkinsons disease, and hypertension.

Some substituted N-acyl aminothiazoles are known in the art, for example, indenothiazolyl phosphonates have been disclosed in U.S. Pat. No. 5,480,874; 2-amino-6-hydroxybenzothiazoles in U.S. Pat. No. 4,929,623; 2-benzoylaminonaphtho[1,2-d]thiazoles in Synthetic Communications (1993), 23(17), 2347-53; benzamido- and 2-acetamidobenzothiazole derivatives in Indian Drugs, (1985), 23(3), 146-51 and certain acylaminothiazole derivatives in U.S. Pat. No. 5,189,049. In U.S. Pat. No. 4,877,876 there are disclosed 2-substituted-8H-indeno(1,2-d)-thiazole derivatives which are similar to the presently claimed compounds.

SUMMARY OF THE INVENTION

The present invention provides at least one compound selected from a compound of formula I

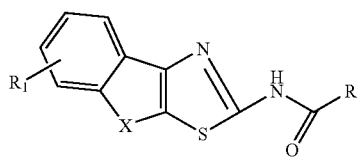

or a pharmaceutically acceptable salt thereof, wherein
X is —$CH_2$—, —$CH_2CH_2$—, —CHCH—, —$(CH_2)_3$— and —O($CH_2$)—;

R is an alkyl group, an alkenyl group, —NHR' or a 5- or 6-membered saturated or unsaturated carbocyclic or heterocyclic ring which optionally may contain one or more hetero atoms and said rings being optionally substituted with one or more substituents selected from the group consisting of halogen, hydroxy, lower alkyl, acetamidomethyl, alkoxycarbonyl amidomethyl, a nitrile group, a sulfonamido group, alkylsulfonyl, alkoxy, benzyl, benzoyl, arylsulfonyl and acyl which benzyl, benzoyl, or arylsulfonyl is optionally substituted by halogen, trihalo lower alkyl, lower alkyl, alkoxy, alkylsulfonyl or cyano;

R' is an alkyl group or a 5- or 6-membered saturated or unsaturated carbocyclic or heterocyclic ring which optionally may contain one or more hetero atoms and said rings being optionally substituted with one or more substituents selected from the group consisting of halogen, lower alkyl, a nitrile group, alkylsulfonyl, alkoxy and acyl and $R_1$ is selected from the group consisting of hydrogen, halogen, lower alkyl, alkoxy or a nitrile group.

The compounds according to this invention show primary activity as Adenosine A2B antagonists and may therefore be useful for the treatment of diseases mediated said receptor. The compounds of the present invention may be used as active agents in the prevention and therapy of, for example, diabetes, diabetic retinopathy, asthma and diarrhea. Secondary antagonism of Adenosine A1 and A2A receptors leads to the compound's use in depression, Parkinson's disease and hypertension.

Objects of the present invention are the compounds of formula I and pharmaceutically acceptable salts and their enantiomeric forms, the preparation of the above mentioned compounds, medicaments containing them and their manufacture as well as methods for using the above mentioned compounds in the control or prevention of illnesses, especially of illnesses and disorders as mentioned above or in the manufacture of corresponding medicaments.

DETAILED DESCRIPTION OF THE INVENTION

The present invention relates to compounds of the formula

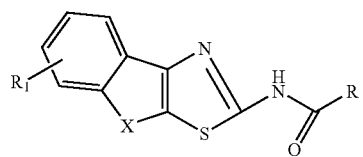

or a pharmaceutically acceptable salt thereof, wherein
X is —$CH_2$—, —$CH_2CH_2$—, —CHCH—, —$(CH_2)_3$— and —$O(CH_2)$—;

R is an alkyl group, an alkenyl group, —NHR' or a 5- or 6-membered saturated or unsaturated carbocyclic or heterocyclic ring which optionally may contain one or more hetero atoms and said rings being optionally substituted with one or more substituents selected from the group consisting of halogen, hydroxy, lower alkyl, acetamidomethyl, alkoxycarbonyl amidomethyl, a nitrile group, a sulfonamido group, alkylsulfonyl, alkoxy, benzyl, benzoyl, arylsulfonyl and acyl which benzyl, benzoyl, or arylsulfonyl is optionally substituted by halogen, trihalo lower alkyl, lower alkyl, alkoxy, alkylsulfonyl or cyano;

R' is an alkyl group or a 5- or 6-membered saturated or unsaturated carbocyclic or heterocyclic ring which optionally may contain one or more hetero atoms and said rings being optionally substituted with one or more substituents selected from the group consisting of halogen, lower alkyl, a nitrile group, alkylsulfonyl, alkoxy and acyl and $R_1$ is selected from the group consisting of hydrogen, halogen, lower alkyl, alkoxy or a nitrile group.

Preferred compounds are those of the formula

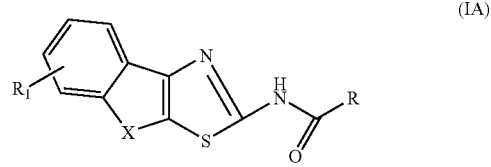

or a pharmaceutically acceptable salt thereof, wherein
X is —$CH_2$—, —$CH_2CH_2$—, —CHCH—, —$(CH_2)_3$— and $O(CH_2)$—;

R is an alkyl group or a 5- or 6-membered saturated or unsaturated carbocyclic or heterocyclic ring which optionally may contain one or more hetero atoms and said rings being optionally substituted with one or more substituent selected from the group consisting of halogen, lower-alkyl, a nitrile group, alkylsulfonyl, alkoxy and acyl.

Also preferred are compounds wherein $R_1$ is hydrogen, halogen or lower-alkoxy.

Further preferred are compounds wherein R is lower-alkyl, lower-alkenyl, phenyl or a heterocyclic ring selected from the group consisting of thienyl, pyridinyl, pyrazolyl, imidazolyl, furyl or piperidinyl, which phenyl or heterocyclic ring is optionally substituted with 1 to 3 substituents selected from the group consisting of halogen, hydroxy, nitrile, lower-alkyl, sulfonamido, lower-alkyl-sulfonyl, lower-alkoxy-carbonyl, lower-alkoxy-C(O)—NH—$CH_2$—, benzyl which is optionally substituted with $CF_3$, benzoyl which is optionally substituted with $CF_3$, or phenylsulfonyl which is optionally substituted with $CF_3$.

Further preferred compounds of formula I are those wherein X is —$CH_2$.

Other preferred compounds as defined above are those, wherein R is lower-alkenyl or a heterocyclic ring selected from the group consisting of thienyl, pyridinyl, pyrazolyl, imidazolyl, fury or piperidinyl, which heterocyclic ring is optionally substituted with 1 to 3 substituents selected from the group consisting of halogen, hydroxy, nitrile, lower-alkyl, sulfonamido, lower-alkyl-sulfonyl, lower-alkoxy-carbonyl, lower-alkoxy-C(O)—NH—$CH_2$—, benzyl which is optionally substituted with $CF_3$, benzoyl which is optionally substituted with $CF_3$, or phenylsulfonyl which is optionally substituted with $CF_3$.

In the compounds of formula (I) as defined above, it is preferred that R is not phenyl, 4-$NO_2$-phenyl or 4-Cl-phenyl, particularly if X is —$CH_2$— and $R_1$ is hydrogen. Furthermore, in the compounds of formula (I) as defined above, it is preferred that R is not phenyl, 4-$NO_2$-phenyl or 4-Cl-phenyl, particularly if X is —$CH_2CH_2$— and $R_1$ is hydrogen or alkoxy. Furthermore, in the compounds of formula (I) as defined above, it is preferred that R is not alkyl, particularly if X is —$CH_2CH_2$— and $R_1$ is hydrogen.

Especially preferred compounds include:
N-(8H-Indeno[1,2-d]thiazol-2-yl)-benzamide;
4-Fluoro-N-(8H-indeno[1,2-d]thiazol-2-yl)-benzamide;
4-Cyano-N-(8H-indeno[1,2-d]thiazol-2-yl)-benzamide;
N-(8H-indeno[1,2-d]thiazol-2-yl)-4-methyl-benzamide;

Thiophene-2-carboxylic acid (8H-indeno[1,2-d]thiazol-2-yl)-amide;
N-(8H-indeno[1,2-d]thiazol-2-yl)nicotinamide;
N-(8H-indeno[1,2-d]thiazol-2-yl)isonicotinamide;
2-Methyl-2H-pyrazole-3-carboxylic acid (8H-indeno[1,2-d]thiazol-2-yl)-amide;
N-(6-chloro-8H-indeno[1,2-d]thiazol-2-yl)-isonicotinamide;
1H-Pyrazole-4-carboxylic acid (8H-indeno[1,2-d]thiazol-2-yl)-amide;
N-(4,5-Dihydro-naphtho[1,2-d]thiazol-2-yl)-isonicotinamide;
N-(5,6-Dihydro-4H-3-thia-1-aza-benzo[e]azulen-2-yl)-isonicotinamide;
N-(4H-Chromeno[4,3-d]thiazol-2-yl)-isonicotinamide;
N-Naphtho[1,2-d]thiazol-2-yl-isonicotinamide;
3-Methyl-3H-imidazole-4-carboxylic acid (8H-indeno[1,2-d]thiazol-2-yl)-amide trifluoroacetate;
4-(8H-Indenol[1,2-d]thiazol-2-ylcarbamoyl)-piperidine-1-carboxylic acid tert-butyl ester;
3-(trifluoromethyl-benzoyl)-piperidine-4-carboxylic acid (8H-indeno[1,2-d]thiazol-2-yl)-amide;
1-(3-trifluoromethyl-benzyl)-piperidine-4-carboxylic acid (9H-indeno[1,2-d]thiazol-2-yl)-amide;
1-(3-Trifluoromethyl-benzenesulfonyl)-piperidine-4-carboxylic acid (8H-indeno[1,2-d]thiazol-2-yl-amide;
N-(8H-Indeno[1,2-d]thiazol-2-yl) 3-fluorobenzamide;
N-(8H-Indeno[1,2-d]thiazol-2-yl) 3-hydroxybenzamide;
N-(8H-Indeno[1,2-d]thiazol-2-yl) 2-methylpent-5-enoylamide;
N-(8H-Indeno[1,2-d]thiazol-2-yl) 2-methylbutanoylamide;
N-(8H-Indeno[1,2-d]thiazol-2-yl) 5-methylsulfonylthiophene-2-carboxyamide;
N-(8H-Indeno[1,2-d]thiazol-2-yl) 2-furoylamide;
N-(6-Fluoro-8H-Indeno[1,2-d]thiazol-2-yl) 4-hydroxynicotinamide;
N-(6-Fluoro-8H-Indeno[1,2-d]thiazol-2-yl) (4-aminosulfonyl)benzamide;
N-(6-Fluoro-8H-Indeno[1,2-d]thiazol-2-yl) (4-t-butoxycarbonylmethyl)benzamide;
N-(6-Fluoro-8H-Indeno[1,2-d]thiazol-2-yl) thiophene-3-carboxyamide;
N-(4,5-Dihydro-naphtho[1,2-d]thiazol-2-yl) 4-hydroxynicotinamide;
N-(4,5-Dihydro-naphtho[1,2-d]thiazol-2-yl) thiophene-3-carboxyamide;
N-(4,5-Dihydro-7-methoxynaphtho[1,2-d]thiazol-2-yl) 4-hydroxynicotinamide;
N-(4,5-Dihydro-7-methoxynaphtho[1,2-d]thiazol-2-yl) 5-methylsulfonylthiophene-2-carboxyamide;
N-(5,6-Dihydro-4H-3-thia-1-aza-benzo[e]azulen-2-yl) 4-hydroxynicotinamide;
N-(5,6-Dihydro-4H-3-thia-1-aza-benzo[e]azulen-2-yl) thiophene-3-carboxyamide;
N-(8H-Indeno[1,2-d]thiazol-2-yl) 3-chloro-4-hydroxybenzamide and
N-(8H-Indeno[1,2-d]thiazol-2-yl) (4-aminosulfonyl)benzamide.

The term "carbocyclic" refers to a 5- or 6-membered saturated or unsaturated carbon containing ring, such as, an aryl ring.

The term "heterocyclic" refers to a 5- or 6-membered ring which can comprise 1, 2 or 3 atoms selected from nitrogen, oxygen and/or sulfur such as tetrahydropyridine, dihydrofuran, dihydropyran, furyl, pyrrolyl, pyridyl, 1,2-, 1,3- and 1,4-diazinyl, thienyl, oxazolyl, oxadiazolyl, isoxazolyl, thiazolyl, isothiazolyl or imidazolyl. A heterocyclic group may be optionally substituted with an aryl group. As noted above the heterocyclic group may be substituted by a variety of substituents and in the case of the benzyl, benzoyl and arylsulfonyl substituents these substituents may be further substituted by halo, trihalo lower alkyl, lower alkyl, alkoxy, alkylsulfonyl or cyano.

The term "halogen" means an atom selected from chlorine, fluorine and bromine.

"Effective amount" means an amount that is effective to prevent, alleviate or ameliorate symptoms of disease or prolong the survival of the subject being treated.

"Hetero atom" means an atom selected from N, O and S.

"$IC_{50}$" refers to the concentration of a particular compound required to inhibit 50% of a specific measured activity. $IC_{50}$ can be measured, inter alia, as is described subsequently.

"Alkyl" denotes a straight-chained or branched saturated aliphatic hydrocarbon.

"Lower alkyl" groups denote C1-C6 alkyl groups and include methyl, ethyl, propyl, isopropyl, butyl, t-butyl, 2-butyl, pentyl, hexyl, and the like. Generally, lower alkyl is preferably C1-C4 alkyl, and more preferably C1-C3 alkyl.

"Alkenyl" groups refer to a straight-chain or branched hydrocarbon residue comprising an olefinic bond and up to 7, preferably up to 4 carbon atoms, such as e.g. 2-propenyl "Aryl" means a monovalent, monocyclic or bicyclic, aromatic carbocyclic hydrocarbon radical, preferably a 5 to 6 membered aromatic ring system. An example of such a radical is phenyl.

"Acyl " denotes —C(O)—$C_1$-$C_6$-alkyl, —C(O)H or C(O)—O alkyl.

"Alkoxy" denotes —O-alkyl. "Lower alkoxy" denotes —O-lower alkyl.

"Pharmaceutically acceptable ester" refers to a conventionally esterified compound of formula I having a carboxyl group, which esters retain the biological effectiveness and properties of the compounds of formula I and are cleaved in vivo (in the organism) to the corresponding active carboxylic acid.

Information concerning esters and the use of esters for the delivery of pharmaceutical compounds is available in Design of Prodrugs. Bundgaard H ed. (Elsevier, 1985). See also, H. Ansel et. al., Pharmaceutical Dosage Forms and Drug Delivery Systems (6th Ed. 1995) at pp.108-109; Krogsgaard-Larsen, et. al., Textbook of Drug Design and Development (2d Ed. 1996) at pp. 152-191.

"Pharmaceutically acceptable salt" refers to conventional acid-addition salts or base-addition salts that retain the biological effectiveness and properties of the compounds of the present invention and are formed from suitable non-toxic organic or inorganic acids or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Sample base-addition salts include those derived from ammonium, potassium, sodium and, quaternary ammonium hydroxides, such as for example, tetramethylammonium hydroxide. Chemical modification of a pharmaceutical compound (i.e. drug) into a salt is a technique well known to pharmaceutical chemists to obtain improved physical and chemical stability, hygroscopicity, flowability and solubility of compounds. See, e.g., H. Ansel et. al., Pharmaceutical Dosage Forms and Drug Delivery Systems (6th Ed. 1995) at pp. 196 and 1456-1457.

"Pharmaceutically acceptable," such as pharmaceutically acceptable carrier, excipient, etc., means pharmacologically acceptable and substantially non-toxic to the subject to which the particular compound is administered.

"Substituted" means that the substitution can occur at one or more positions and, unless otherwise indicated, that the substituents at each substitution site are independently selected from the specified options.

The invention therefore also relates to pharmaceutical compositions comprising a compound as defined above and a pharmaceutically acceptable carrier and/or adjuvant.

The compounds of formula (I) can be manufactured by the methods given below, by the methods given in the examples or by analogous methods. Appropriate reaction conditions for the individual reaction steps are known to the person skilled in the art. Starting materials are either commercially available or can be prepared by methods analogous to the methods given below or in the examples or by methods known in the art.

The compounds of formula I and/or their pharmaceutically acceptable salts can be used as medicaments, e.g. in the form of pharmaceutical preparations for enteral, parenteral or topical administration. They can be administered, for example, perorally, e.g. in the form of tablets, coated tablets, dragées, hard and soft gelatine capsules, solutions, emulsions or suspensions, rectally, e.g. in the form of suppositories, parenterally, e.g. in the form of injection solutions or infusion solutions, or topically, e.g. in the form of ointments, creams or oils. Oral administration is preferred.

The production of the pharmaceutical preparations can be effected in a manner which will be familiar to any person skilled in the art by bringing the described compounds of formula (I) and/or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatine capsules. Suitable carrier materials for soft gelatine capsules are, for example, vegetable oils, waxes, fats and semi-solid and liquid polyols (depending on the nature of the active ingredient no carriers might, however, be required in the case of soft gelatine capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives. Usual stabilizers, preservatives, wetting and emulsifying agents, consistency-improving agents, flavor-improving agents, salts for varying the osmotic pressure, buffer substances, solubilizers, colorants and masking agents and antioxidants come into consideration as pharmaceutical adjuvants.

The dosage of the compounds of formula (I) can vary within wide limits depending on the disease to be controlled, the age and the individual condition of the patient and the mode of administration, and will, of course, be fitted to the individual requirements in each particular case. For adult patients a daily dosage of about 1 to 1000 mg, especially about 1 to 100 mg, comes into consideration. Depending on severity of the disease and the precise pharmacokinetic profile the compound could be administered with one or several daily dosage units, e.g. in 1 to 4 dosage units.

The following reaction scheme and narrative therewith sets forth the general methodology for making the novel compounds of the present invention.

Scheme 1:

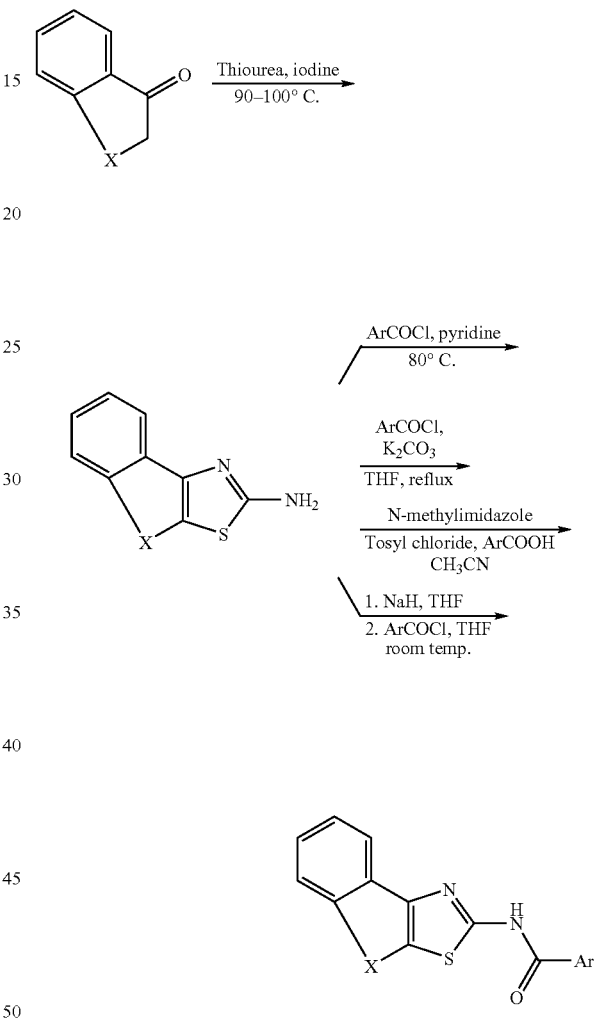

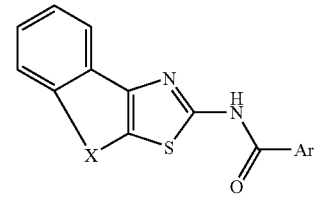

Description of Scheme 1:

Heating a mixture of the appropriate ketone I with thiourea and iodine to 90-100° C. in the absence of solvent provided the thiazole intermediates II. Acylation of II with an aroyl or heteroaroyl chloride in the presence of a base such as potassium carbonate or pyridine with heating provided the acyl products III. Alternatively, deprotonation of II with a stong base such as sodium hydride followed by acylation with the aroyl or heteroaroyl chloride also gave rise to the acyl products III. Compounds of structure III may also be prepared via coupling of amine II with aryl carboxylic acids using O-(7-Azabenzotriazol-1-yl)-N,N,N',N'-tetramethyluronium hexafluorophosphate (HATU) or a combination of p-toluenesulfonyl chloride and N-methylimidazole as coupling agents.

Scheme 2:

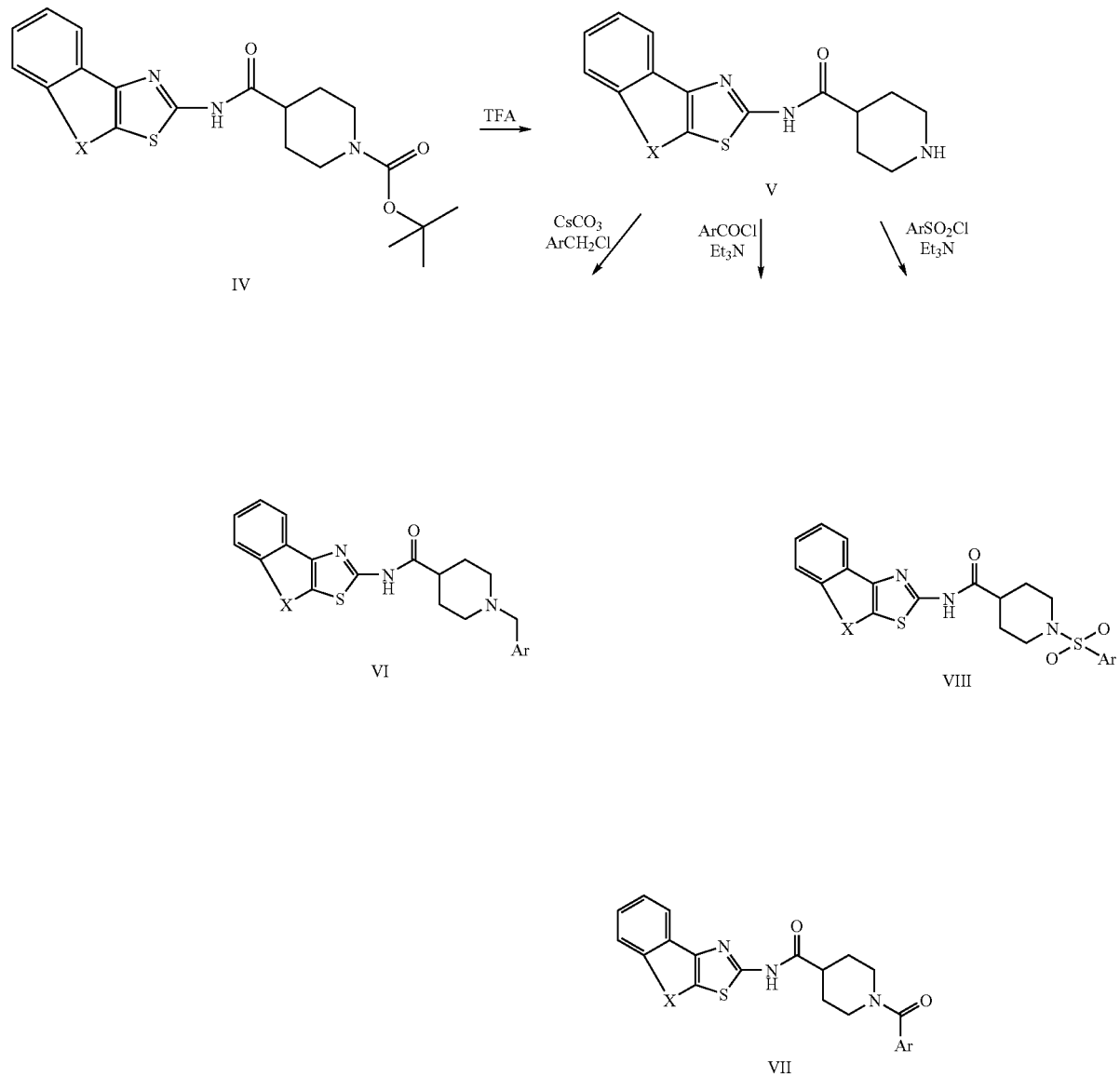

Description of Scheme 2:

Deprotection of compound IV with trifluoroacetic acid provides the intermediate piperidine compound V. Compound V may then be reacted with a suitable aryl halide, benzoyl halide or arylsulfonyl halide in the presence of a base such as triethyl amine to provide compounds VI, VII and VIII.

The reaction conditions for the above reactions can vary to a certain extent. Methods to perform the above described reactions and processes are known in the art or can be deduced in analogy from the examples. Starting materials are commercially available or can be made by methods analogous to those described in the examples.

The following examples shall illustrate preferred embodiments of the present invention but are not intended to limit the scope of the invention.

EXAMPLE 1

N-(8H-Indeno[1,2-d]thiazol-2-yl)-benzamide

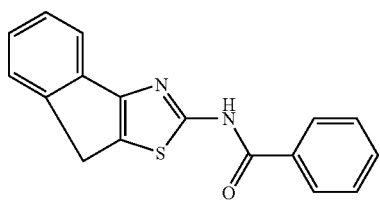

Step 1: 8H-Indeno[1,2-d]thiazol-2-ylamine hydroiodide

A mixture of 1-indanone (6.00 g; 45.4 mmol), thiourea (6.92 g; 90.8 mmol) and iodine (11.52 g; 45.4 mmol) was heated to 95° C. with stirring. After 3 hours, the mixture was allowed to cool to room temperature. The crude solid was triturated with absolute ethanol and filtered. The light yellow solid was washed twice with absolute ethanol then allowed to air dry to provide 9.13 g of 8H-Indeno[1,2-d]thiazol-2-ylamine hydroiodide 1a.

Step 2: 8H-Indeno[1,2-d]thiazol-2-ylamine

Indeno[1,2-d]thiazol-2-ylamine hydroiodide 1a (9.13 g) was stirred with 100 mL of 1N sodium hydroxide for 1 hour at room temperature then filtered. The solid was washed with water (3×20 mL) and then allowed to air dry to provide 5.30 g of 8H-Indeno[1,2-d]thiazol-2-ylamine 1b.

Step 3: N-(8H-Indeno[1,2-d]thiazol-2-yl)-benzamide

To a mixture of Indeno[1,2-d]thiazol-2-ylamine hydroiodide 1a (100 mg; 0.32 mmol) in pyridine (2 mL) was added benzoyl chloride (0.12 mL; 0.96 mmol) dropwise. The mixture was then agitated at 80° C. in a sealed tube overnight. The mixture was allowed to cool to room temperature and the solvent removed in vacuo. The residue was taken up into ethyl acetate and the extract allowed to stir with 2M sodium carbonate solution for 2 hours at room temperature. The organic layer was then washed with brine solution, dried over sodium sulfate and concentrated in vacuo. The crude product was chromatographed on silica gel (eluent: 10% ethyl acetate/hexanes to 40% ethyl acetate gradient) to provide 53 mg of N-(8H-Indeno[1,2-d]thiazol-2-yl)-benzamide 2. EI-HRMS m/e calcd for $C_{17}H_{12}N_2OS$ 292.0670, found 292.0666.

EXAMPLE 2

4-Fluoro-N-(8H-indeno[1,2-d]thiazol-2-yl)-benzamide

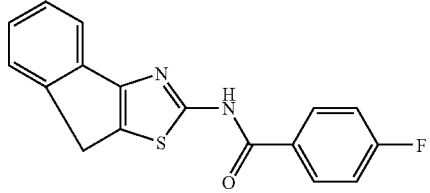

Acylation of 8H-Indeno[1,2-d]thiazol-2-ylamine hydroiodide 1a (Prepared in Example 1, Step 1, 100 mg; 0.32 mmol) with 4-fluorobenzoyl chloride (0.116 mL; 0.96 mmol) in a manner similar to that described in Example 1, Step 3 provided 35 mg of 4-Fluoro-N-(8H-indeno[1,2-d]thiazol-2-yl)-benzamide 3. EI-HRMS m/e calcd for $C_{17}H_{11}FN_2OS$ 310.0576, found 310.0577.

EXAMPLE 3

4-Cyano-N-(8H-indeno[1,2-d]thiazol-2-yl)-benzamide

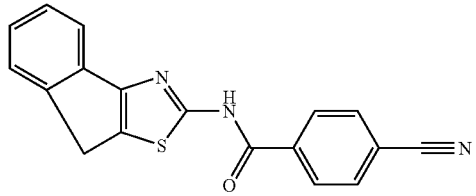

Acylation of 8H-Indeno[1,2-d]thiazol-2-ylamine hydroiodide 1a (Prepared in Example 1, Step 1, 100 mg; 0.32 mmol) with 4-cyanobenzoyl chloride (164 mg; 0.96 mmol) in a manner similar to that described in Example 1, Step 3 provided 26 mg of 4-Cyano-N-(8H-indeno[1,2-d]thiazol-2-yl)-benzamide 4. EI-HRMS m/e calcd for $C_{18}H_{14}N_2OS$ (M$^+$) 306.0827, found 306.0827.

EXAMPLE 4

N-(8H-Indeno[1,2-d]thiazol-2-yl)-4-methyl-benzamide

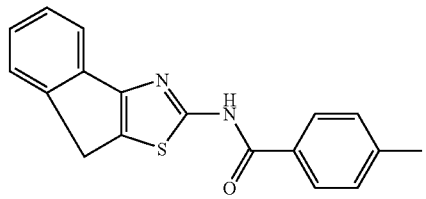

Acylation of 8H-Indeno[1,2-d]thiazol-2-ylamine hydroiodide 1a (Prepared in Example 1, Step 1, 100 mg; 0.32 mmol) with 4-methylbenzoyl chloride (0.0.130 mL; 0.96 mmol) in a manner similar to that described in Example 1, Step 3 provided 25 mg of N-(8H-Indeno[1,2-d]thiazol-2-yl)-4-methyl-benzamide 5. EI-HRMS m/e calcd for $C_{16}H_{11}N_3OS$ (M$^+$) 293.0623, found 293.0621.

EXAMPLE 5

Thiophene-2-carboxylic acid (8H-indeno[1,2-d]thiazol-2-yl)-amide

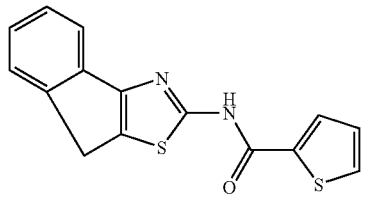

Acylation 8H-Indeno[1,2-d]thiazol-2-ylamine hydroiodide 1a (Prepared in Example 1, Step 1, 100 mg; 0.32 mmol) with 2-thiophenecarbonyl chloride (0.106 mL; 0.96 mmol) in a manner similar to that described in Example 1, Step 3 provided 17 mg of Thiophene-2-carboxylic acid (8H-indeno[1,2-d]thiazol-2-yl)-amide 6. EI-HRMS m/e calcd for $C_{15}H_{10}N_2OS_2$ (M$^+$) 298.0235, found 298.0233.

EXAMPLE 6

N-(8H-Indeno[1,2-d]thiazol-2-yl)-nicotinamide

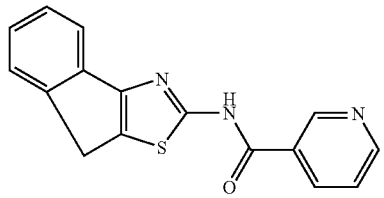

A suspension of 8H-Indeno[1,2-d]thiazol-2-ylamine hydroiodide 1a (Prepared in Example 1, Step 1, mg; mmol), nicotinoyl chloride hydrochloride (92 mg; 0.50 mmol) and diisopropylethylamine (0.50 mL; 2.77 mmol) in dichloroethane was heated in a sealed tube to 120° C. in a microwave oven for 10 minutes. The mixture was allowed to cool to room temperature and the solvent removed in vacuo. The residue was taken up into 2 M sodium carbonate solution and extracted with ethyl acetate. The extracts were dried (sodium sulfate), filtered and concentrated in vacuo. The crude product was chromatographed on silica gel (eluent=50% ethyl acetate/hexanes to 100% ethyl acetate/hexanes gradient) to provide 43 mg of N-(8H-Indeno[1,2-d]thiazol-2-yl)-nicotinamide 7. EI-HRMS m/e calcd for $C_{16}H_{11}N_4OS$ ($M^+$) 293.0623, found 293.0620.

EXAMPLE 7

N-(8H-Indeno[1,2-d]thiazol-2-yl)-isonicotinamide

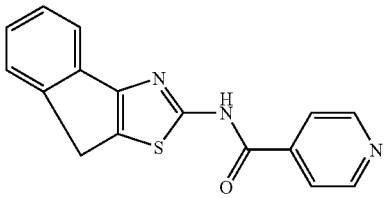

To a mixture of 8H-Indeno[1,2-d]thiazol-2-ylamine 1b (Prepared in Example 1, Step 2, 640 mg; 3.4 mmol) and potassium carbonate (5.40 g; 39.1 mmol) in dry tetrahydrofuran (20 mL) under nitrogen was added isonicotinoyl chloride hydrochloride (959 mg; 5.10 mmol). The slurry was then heated to reflux for 18 hr. At this point, potassium carbonate (5.40 g; 39.1 mmol) and isonicotinoyl chloride hydrochloride (959 mg; 5.10 mmol) were added and reflux continued for 22 hr., then allowed to cool to room temperature. The solvent was removed in vacuo and the residue diluted with water and extracted with methylene chloride. The insoluble material was filtered off and washed methylene chloride and water and finally triturated with diethyl ether to provide 253 mg of N-(8H-Indeno[1,2-d]thiazol-2-yl)-isonicotinamide 8. EI-HRMS m/e calcd for $C_{16}H_{11}N_3OS$ ($M^+$) 293.0623, found 293.0621.

EXAMPLE 8

2-Methyl-2H-pyrazole-3-carboxylic acid (8H-indeno[1,2-d]thiazol-2-yl)-amide

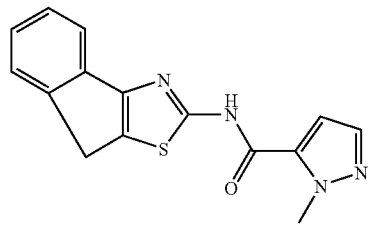

To a mixture 8H-Indeno[1,2-d]thiazol-2-ylamine 1b (Prepared in Example 1, Step 2, 320 mg; 1.70 mmol) and potassium carbonate (3.10 g; 22.4 mmol) in dry tetrahydrofuran (10 mL) under nitrogen was added 2-methyl-2H-pyrazole-3-carbonyl chloride (516 mg; 3.57 mmol). The slurry was then heated to reflux for 3 hr. The solvent was removed in vacuo, and the residue diluted with water and extracted with ethyl acetate. The organic layer was washed with 50 mL of 1N hydrochloric acid solution followed by brine solution and dried (sodium sulfate) filtered and concentrated in vacuo. The crude product was purified by trituration with diethyl ether to provide 155 mg of 2-Methyl-2H-pyrazole-3-carboxylic acid (8H-indeno[1,2-d]thiazol-2-yl)-amide 9. EI-HRMS m/e calcd for $C_{15}H_{12}N_4OS$ ($M^+$) 296.0732, found 296.0731.

EXAMPLE 9

N-(6-Chloro-8H-indeno[1,2-d]thiazol-2-yl)-isonicotinamide

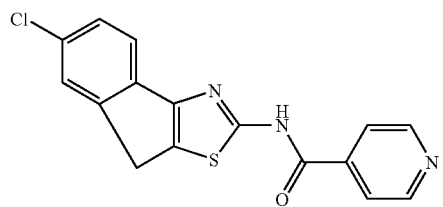

Step 1: 6-Chloro-8H-indeno[1,2-d]thiazol-2-ylamine hydroiodide

A mixture of 5-chloro-1-indanone (1.00 g; 6.00 mmol), thiourea (0.917 g; 12.0 mmol) and iodine (1.55 g; 6.10 mmol) was heated to 100° C. in a sealed tube. After 1 hr., the mixture was allowed to cool to room temperature. The solid was triturated with water and filtered. The solid was then triturated with absolute ethanol, filtered and washed several times with absolute ethanol to provide 0.60 g of 6-Chloro-8H-indeno[1,2-d]thiazol-2-ylamine hydroiodide 10.

Step 2: N-(6-Chloro-8H-indeno[1,2-d]thiazol-2-yl)-isonicotinamide

A mixture of 6-Chloro-8H-indeno[1,2-d]thiazol-2-ylamine hydroiodide 10 (80 mg; 0.23 mmol), potassium carbonate (138 mg; 1.0 mmol) and isonicotinoyl chloride hydrochloride (89 mg; 0.5 mmol) in dry tetrahydrofuran was heated to 80° C. in a sealed tube. After 20 hr., the mixture was allowed to cool to room temperature and concentrated in vacuo. The residue was diluted with methylene chloride and washed with water. The organic layer was dried (sodium sulfate), filtered and concentrated in vacuo. The crude product was purified by reverse phase HPLC (eluent: acetonitrile/water/0.1% trifluoroacetic acid) to provide 20 mg of N-(6-Chloro-8H-indeno[1,2-d]thiazol-2-yl)-isonicotinamide 11 as the trifluoroacetate salt. EI-HRMS m/e calcd for $C_{16}H_{10}ClN_3OS$ (M$^+$) 327.0233, found 327.0217.

EXAMPLE 10

1H-Pyrazole-4-carboxylic acid (8H-indeno[1,2-d]thiazol-2-yl)-amide

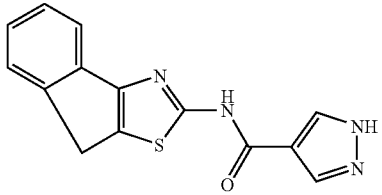

Step 1: 4-pyrazolecarbonyl chloride

A mixture of 4-pyrazolecarboxylic acid (600 mg) in thionyl chloride (5 mL) was heated to 90° C. under nitrogen. After 18 hr., the mixture was allowed to cool to room temperature and the solvent removed in vacuo to provide 579 mg of 4-pyrazolecarbonyl chloride 12, which was used without further purification for the next step (Step 2). EI-HRMS m/e calcd for $C_{16}H_{11}N_3OS$ (M$^+$) 293.0623, found 293.0621.

Step 2: 1H-Pyrazole-4-carboxylic acid (8H-indeno[1,2-d]thiazol-2-yl)-amide

Acylation 8H-Indeno[1,2-d]thiazol-2-ylamine 1b (Prepared in Example 1, Step 2, 377 mg; 2.00 mmol) with 4-pyrazolecarbonyl chloride 12 (208 mg; 1.6 mmol) in a manner similar to that described in Example 7, provided 190 mg of 1H-Pyrazole-4-carboxylic acid (8H-indeno[1,2-d]thiazol-2-yl)-amide 13 as a dark powder.

EXAMPLE 11

3-Methyl-3H-imidazole-4-carboxylic acid (8H-indeno[1,2-d]thiazol-2-yl)-amide trifluoroacetate

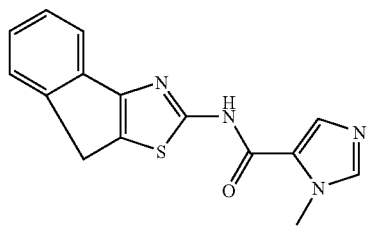

To a mixture of 8H-Indeno[1,2-d]thiazol-2-ylamine 1b (Prepared in Example 1, Step 2, 94 mg; 0.50 mmol), 1-methyl-1H-imidazole-5-carboxylic acid (65 mg; 0.50 mmol) and BOP reagent (443 mg; 1.0 mmol) in dry methylene chloride at room temperature was added diisopropylethyl amine (0.55 mL; 3.13 mmol) dropwise. After 96 hours, the reaction mixture was diluted with methylene chloride and washed with water followed by brine solution. The organic layer was dried (sodium sulfate) filtered and concentrated in vacuo. Purification using reverse phase HPLC (eluent: acetonitrile/water/0.1% trifluoroacetic acid) provided 70 mg of 14. EI-HRMS m/e calcd for $C_{15}H_{12}N_4OS$ (M$^+$) 296.0732, found 296.0728.

EXAMPLE 12

N-(4,5-Dihydro-naphtho[1,2-d]thiazol-2-yl)-isonicotinamide

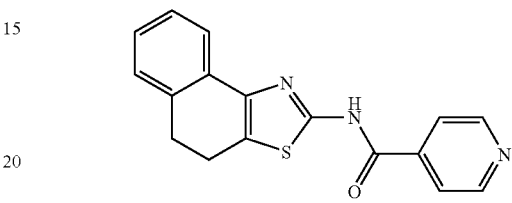

Step 1: 4,5-Dihydro-naphtho[1,2-d]thiazol-2-ylamine hydroiodide

A mixture of 1-tetralone (5.00 mL; 37.6 mmol), thiourea (5.72 g; 75.2 mmol) and iodine (9.54 g; 37.6 mmol) were heated to 95° C. with stirring. After 4 hr., the mixture solidified and was allowed to cool to room temperature. The mixture was diluted with 200 mL of water and the solid material was filtered off and triturated with absolute ethanol. The solid was washed several times with absolute ethanol to provide 4.00 g of 4,5-Dihydro-naphtho[1,2-d]thiazol-2-ylamine hydroiodide 15 as an off white powder.

Step 2: N-(4,5-Dihydro-naphtho[1,2-d]thiazol-2-yl)-isonicotinamide

Added sodium hydride (26 mg; 1.1 mmol) to a stirred suspension of 4,5-Dihydro-naphtho[1,2-d]thiazol-2-ylamine hydroiodide 15 in dry tetrahydrofuran under nitrogen at room temperature. After 15 minutes, isonicotinoyl chloride hydrochloride (107 mg; 0.60 mmol) was added and the mixture allowed to stir for 2 hr. at room temperature and then concentrated in vacuo. The residue was diluted with water the solid material was filtered off. Purification using reverse phase HPLC (eluent: acetonitrile/water/0.1% trifluoroacetic acid) provided 20 mg of N-(4,5-Dihydro-naphtho[1,2-d]thiazol-2-yl)-isonicotinamide 16 as the trifluoroacetate salt. ES-HRMS m/e calcd for $C_{17}H_{13}N_3OS$ (M+H) 308.0852, found 308.0851.

EXAMPLE 13

N-(5,6-Dihydro-4H-3-thia-1-aza-benzo[e]azulen-2-yl)-isonicotinamide

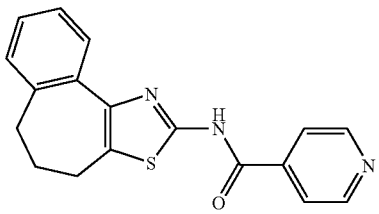

Step 1: 5,6-Dihydro-4H-3-thia-1-aza-benzo[e]azulen-2-ylamine hydroiodide

A mixture of 1-benzosuberone (1.00 mL; 6.7 mmol), thiourea (1.02 g; 13.4 mmol) and iodine (1.70 g; 6.7 mmol) were heated to 95° C. with stirring. After 20 hr., the mixture was allowed to cool to room temperature, diluted with 200 mL of water, the solid material filtered off washed twice with 25 mL of water followed by diethyl ether (3×20 mL) to provide 1.50 g of 5,6-Dihydro-4H-3-thia-1-aza-benzo[e]azulen-2-ylamine hydroiodide 17 as an off white powder.

Step 2: N-(5,6-Dihydro-4H-3-thia-1-aza-benzo[e]azulen-2-yl)-isonicotinamide

Added sodium hydride (17 mg; 0.7 mmol) to a stirred suspension of 5,6-Dihydro-4H-3-thia-1-aza-benzo[e]azulen-2-ylamine hydroiodide 17 (80 mg; 0.23 mmol) in dry tetrahydrofuran under nitrogen at room temperature. After 15 minutes, isonicotinoyl chloride hydrochloride (62 mg; 0.35 mmol) was added and the mixture allowed to stir for 1 hr. at room temperature and then concentrated in vacuo. The residue was triturated with water the solid material was filtered off. Purification using reverse phase HPLC (eluent: acetonitrile/water/0.1% trifluoroacetic acid) provided 20 mg of N-(5,6-Dihydro-4H-3-thia-1-aza-benzo[e]azulen-2-yl)-isonicotinamide 18 as the trifluoroacetate salt. EI-HRMS m/e calcd for $C_{18}H_{15}N_3OS$ (M+) 321.0936, found 321.0935.

EXAMPLE 14

N-(4H-Chromeno[4,3-d]thiazol-2-yl)-isonicotinamide

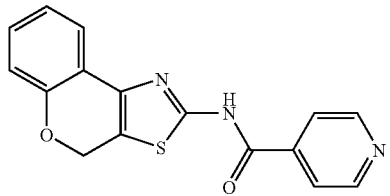

Step 1: 4H-Chromeno[4,3-d]thiazol-2-ylamine hydroiodide

A mixture of 4-chromanone (2.00 g; 13.5 mmol), thiourea (2.06 g; 27.0 mmol) and iodine (3.43 g; 13.5 mmol) were heated to 95° C. with stirring. After 4.5 hr., the mixture was allowed to cool to room temperature, triturated with methylene chloride, the solid material filtered off. The solid was further triturated with ethyl acetate, filtered and washed with ethyl acetate to provide 3.00 g of 4H-Chromeno[4,3-d]thiazol-2-ylamine hydroiodide 19 as an off white powder.

Step 2: N-(4H-Chromeno[4,3-d]thiazol-2-yl)-isonicotinamide

Added sodium hydride (19 mg; 0.8 mmol) to a stirred suspension of 4H-Chromeno[4,3-d]thiazol-2-ylamine hydroiodide 19 (90 mg; 0.27 mmol) in dry tetrahydrofuran under nitrogen at room temperature. After 15 minutes, isonicotinoyl chloride hydrochloride (62 mg; 0.35 mmol) was added and the mixture allowed to stir for 3 hr. at room temperature and then concentrated in vacuo. The residue was diluted with water and extracted with ethyl acetate. The extracts were dried (sodium sulfate), filtered and concentrated in vacuo. Purification using reverse phase HPLC (eluent: acetonitrile/water/0.1% trifluoroacetic acid) provided 12 mg of N-(4H-Chromeno[4,3-d]thiazol-2-yl)-isonicotinamide 20 as the trifluoroacetate salt. ES-HRMS m/e calcd for $C_{16}H_{11}N_3OS$ (M+H) 310.0645, found 310.0646.

EXAMPLE 15

N-Naphtho[1,2-d]thiazol-2-yl-isonicotinamide

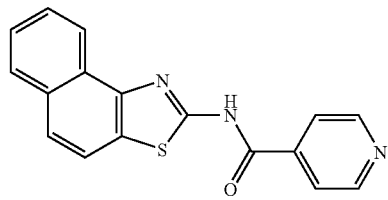

Step 1: Naphtho[1,2-d]thiazol-2-ylamine hydrobromide

Bromine (0.26 mL; 5.14 mmol) was added dropwise to a stirred mixture of 2-naphthalene thiourea (800 mg; 3.96 mmol) in dry methylene chloride (10 mL) at room temperature. The mixture was then heated to reflux. After 2 hr., the mixture was allowed to cool to room temperature. The solid was filtered off and washed several times with methylene chloride to provide 1.12 g of Naphtho[1,2-d]thiazol-2-ylamine hydrobromide 21.

Step 2: N-Naphtho[1,2-d]thiazol-2-yl-isonicotinamide

Added sodium hydride (73 mg; 2.89 mmol) to a stirred suspension of 21 (90 mg; 0.27 mmol) in dry tetrahydrofuran under nitrogen at room temperature. After 30 minutes, isonicotinoyl chloride hydrochloride (150 mg; 0.84 mmol) was added and the mixture allowed to stir for 72 hr. at room temperature. The mixture was concentrated in vacuo, the residue taken up into ethyl acetate and washed with saturated ammonium chloride solution. The organic layer was dried (sodium sulfate), filtered and concentrated in vacuo. Purification using reverse phase HPLC (eluent: acetonitrile/water/0.1% trifluoroacetic acid) provided 26 mg of N-Naphtho[1,2-d]thiazol-2-yl-isonicotinamide 22. ES-HRMS m/e calcd for $C_{17}H_{11}N_3OS$ (M+H) 306.0696, found 306.0691.

EXAMPLE 16

4-(8H-Indenol[1,2-d]thiazol-2-ylcarbamoyl)-piperidine-1-carboxylic acid tert-butyl ester

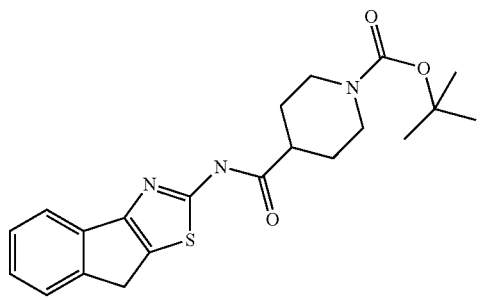

To a magnetically stirred mixture of piperidine-1,4-dicarboxylic acid mono-tert-butyl ester (195 mg, 0.848 mmol) in $CH_3CN$ (10 mL) at room temperature was added 1-methylimidazole (200 mL, 2.52 mmol, Aldrich). The reaction mixture was cooled in an ice bath and then charged with p-toluenesulfonyl chloride (192 mg, 1.01 mmol, Aldrich).

After stirring in the ice bath for 30 minutes, 8H-indeno[1,2-d]thiazol-2-ylamine (160 mg, 0.84 mmol) was added. The ice bath was removed, and the reaction mixture was stirred at room temperature for 2 hours. LC/MS analysis indicated complete consumption of starting material. The reaction mixture was filtered and the resulting solids were washed with acetonitrile to give 4-(8H-indenol[1,2-d]thiazol-2-ylcarbamoyl)-piperidine-1-carboxylic acid tert-butyl ester (330 mg, 99% yield) as an off-white solid. HRMS calcd for $C_{21}H_{25}N_3O_3S$ (M+H)$^+$400.169, found 400.169.

EXAMPLE 17

3-(trifluoromethyl-benzoyl)-piperidine-4-carboxylic acid (8H-indeno[1,2-d]thiazol-2-yl)-amide (44 mg, 55.2% yield)

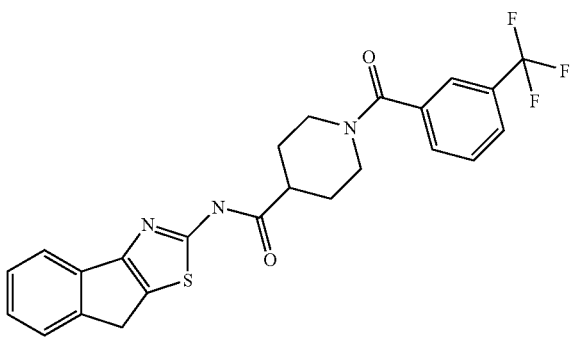

Step 1:

Deprotection of 4-(8H-indenol[1,2-d]thiazol-2-ylcarbamoyl)-piperidine-1-carboxylic acid tert-butyl ester (350 mg, 0.876 mmol) with TFA according to known procedures gave piperidine-4-carboxylic acid (8H-indeno[1,2-d]thiazol-2-yl)-amide TFA salt as a white powder (306 mg, 84.5% yield); HRMS for $C_{16}H_{17}N_3OS$ (M+H)$^+$ at m/z=300.12.

Step 2

To a mixture of piperidine-4-carboxylic acid (8H-indeno[1,2-d]thiazol-2-yl)-amide (70 mg; 0.169 mmol), and triethylamine (59 mL; 0.42 mmol) in 10 mL of methylene chloride at room temperature was added 3-(trifluoromethyl)benozyl chloride (25 mL; 0.169 mmol) dropwise. After 24 hours at room temperature, the reaction mixture was diluted with ethyl acetate and then washed with 1N HCl, saturated. Aq. NaHCO$_3$, water, and brine. The organic layer was dried (sodium sulfate), filtered, and concentrated in vacuo. The crude product was purified by chromatography (gradient elution with 75% ethyl acetate/hexane to 100% ethyl acetate) to furnish 3-(trifluoromethyl-benzoyl)-piperidine-4-carboxylic acid (8H-indeno[1,2-d]thiazol-2-yl)-amide (44 mg, 55.2% yield); HRMS calcd for $C_{24}H_{20}N_3O_3$ $_{(M+H)}$$^+$472.1301, found 472.1301.

EXAMPLE 18

In an analogous manner, there was obtained:
1-(3-Trifluoromethyl-benzenesulfonyl)-piperidine-4-carboxylic acid (8H-indeno[1,2-d]thiazol-2-yl-amide

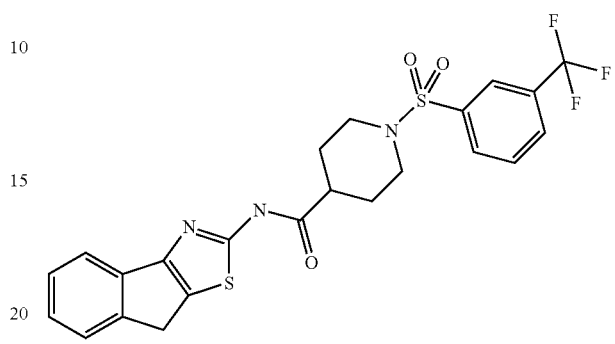

From piperidine-4-carboxylic acid (8H-indeno[1,2-d]thiazol-2-yl)-amide (from Example 17, step 1) (60 mg, 0.145 mmol) and 3-(trifluoromethyl)benzenesulfonyl chloride (42.6 mg, 0.174 mmol) and triethylamine as a white solid (58 mg, 78.9% yield): HRMS calcd for $C_{23}H_{20}N_3O_3F_3S_2$ (M+H)$^+$508.0971, found 508.0971.

EXAMPLE 19

1-(3-trifluoromethyl-benzyl)-piperidine-4-carboxylic acid (9H-indeno[1,2-d]thiazol-2-yl)-amide

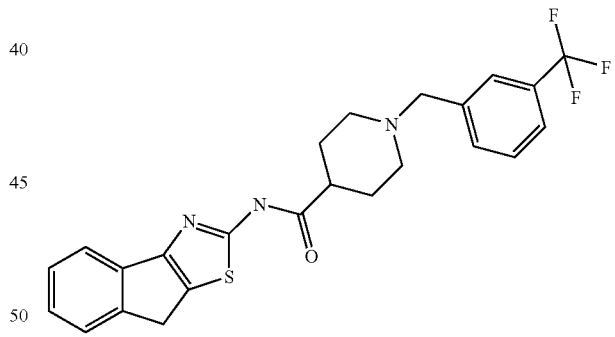

To a magnetically stirred mixture of piperidine-4-carboxylic acid (8H-indeno[1,2-d]thiazol-2-yl)-amide (from Example 17, step 1) (70 mg, 0.169 mmol) in DMF (15 mL, Aldrich) at room temperature was added cesium carbonate (0.5 g, 0.0153 mmol) followed by 3-(trifluoromethyl)benzyl chloride (26 mL, 0.169 mmol, Aldrich). The reaction mixture was stirred at room temperature for 3 hours. The crude reaction mixture was filtered and concentrated. Purification using reverse phase HPLC (eluent: acetonitrile/water/0.1% trifluoroacetic acid) provided 1-(3-trifluoromethyl-benzyl)-piperidine-4-carboxylic acid (9H-indeno [1,2-d]thiazol-2-yl)-amide TFA salt (33 mg, 34.1% yield) as a white solid. HRMS calcd for $C_{24}H_{22}N_3OF_3S$ (M+H)$^+$458.1509, found 458.1506.

EXAMPLE 20

The Product 1-19 amides were prepared following scheme 1 above and the below procedure in a parallel format.

A mixture N-methylpyrrolidin-2-one (NMP) solution of the carboxylic acid (0.3M, 1 ml, 0.3 mmol), O-(7-Azabenzotriazol-1-yl)-N,N,N'N'-tetramethyluronium hexafluorophosphate, HATU (0.3M, 1 ml, 0.3 mmol) and neat diisopropylethylamine (0.05 ml, 0.3 mmol) in a 12 ml tube was shaken for 20 min at RT. Then the aminothiazole in NMP (0.2M, 1 ml, 0.2 mmol) was added. The tube was sealed with a cap and shaken at 90 C for 12 hours. After cooling to room temp., the reaction mixture was diluted with ethyl acetate (2 ml) and sodium hydroxide solution (0.5M, 2 ml). The tubes were vortexed for extraction and centrifuged for layer separation. Organic layers were transferred to 20 ml scintillation vials. The aqueous layers were extracted again with ethyl acetate as above. The scintillation vials containing the combined ethyl acetate extracts were then loaded on a Genevac evaporator to remove all the organic solvents. The crude products were checked by HPLC for purity and then purified by HPLC to give pure amides.

Product 1: N-(8H-Indeno[1,2-d]thiazol-2-yl) 3-fluorobenzamide. 37 mg (60% yield). 100% pure (LR-LCMS, calc. 311.06, found 311.03).

Product 2: N-(8H-Indeno[1,2-d]thiazol-2-yl) 3-hydroxybenzamide. 2 mg (3% yield). 100% pure (LR-LCMS, calc. 309.07, found 309.05).

Product 3: N-(8H-Indeno[1,2-d]thiazol-2-yl) 2-methylpent-5-enoylamide. 31 mg (55% yield). 100% pure (LR-LCMS, calc. 285.1, found 285.08).

Product 4: N-(8H-Indeno[1,2-d]thiazol-2-yl) 2-methylbutanoylamide. 28 mg (51% yield). 100% pure (LR-LCMS, calc. 273.1, found 273.09).

Product 5: N-(8H-Indeno[1,2-d]thiazol-2-yl) 5-methylsulfonylthiophene-2-carboxyamide. 63 mg (84% yield). 100% pure (LR-LCMS, calc. 377.01, found 377.03).

Product 6: N-(8H-Indeno[1,2-d]thiazol-2-yl) 2-furoylamide. 53 mg (95% yield). 100% pure (LR-LCMS, calc. 283.05, found 283.04).

Product 7: N-(6-Fluoro-8H-Indeno[1,2-d]thiazol-2-yl) 4-hydroxynicotinamide. 2 mg (3% yield). 100% pure (LR-LCMS, calc. 328.05, found 328.06).

Product 8: N-(6-Fluoro-8H-Indeno[1,2-d]thiazol-2-yl) (4-aminosulfonyl)benzamide. 7 mg (9% yield). 100% pure (LR-LCMS, calc. 390.03, found 390.03).

Product 9: N-(6-Fluoro-8H-Indeno[1,2-d]thiazol-2-yl) (4-t-butoxycarbonylmethyl)benzamide. 14 mg (16% yield). 100% pure (LR-LCMS, calc. 440.14, found 440.19).

Product 10: N-(6-Fluoro-8H-Indeno[1,2-d]thiazol-2-yl) thiophene-3-carboxyamide. 10 mg (16% yield). 100% pure (LR-LCMS, calc. 317.08, found 317.07).

Product 11: N-(4,5-Dihydro-naphtho[1,2-d]thiazol-2-yl) 4-hydroxynicotinamide. 4 mg (6% yield). 100% pure (LR-LCMS, calc. 234.08, found 324.08).

Product 12: N-(4,5-Dihydro-naphtho[1,2-d]thiazol-2-yl) thiophene-3-carboxyamide. 10 mg (16% yield). 100% pure (LR-LCMS, calc. 213.04, found 313.03).

Product 13: N-(4,5-Dihydro-7-methoxynaphtho[1,2-d]thiazol-2-yl) 4-hydroxynicotinamide. 2 mg (3% yield). 100% pure (LR-LCMS, calc. 354.09, found 354.09).

Product 14: N-(4,5-Dihydro-7-methoxynaphtho[1,2-d]thiazol-2-yl) 5-methylsulfonylthiophene-2-carboxyamide. 15 mg (18% yield). 100% pure (LR-LCMS, calc. 421.03, found 421.02).

Product 16: N-(5,6-Dihydro-4H-3-thia-1-aza-benzo[e]azulen-2-yl) 4-hydroxynicotinamide. 10 mg (15% yield). 100% pure (LR-LCMS, calc. 338.09, found 338.19).

Product 17: N-(5,6-Dihydro-4H-3-thia-1-aza-benzo[e]azulen-2-yl) thiophene-3-carboxyamide. 22 mg (34% yield). 100% pure (LR-LCMS, calc. 327.06, found 327.12).

Product 18: N-(8H-Indeno[1,2-d]thiazol-2-yl) 3-chloro-4-hydroxybenzamide. 16 mg (23% yield). 100% pure (LR-LCMS, calc. 343.03, found 343.07).

Product 19: N-(8H-Indeno[1,2-d]thiazol-2-yl) (4-aminosulfonyl)benzamide. 10 mg (13% yield). 100% pure (LR-LCMS, calc. 372.04, found 373.06).

EXAMPLE 21

Inhibitory Activity on NECA-Induced Cyclic AMP Production in CHO.K1 Cells Expressing Human Adenosine A2B Receptor A Chinese hamster ovary (CHO.K1) cell stably transfected with human adenosine A2B receptor cDNA 4b was used in this assay. Cells were cultured under 5% CO2/95% O2 atmosphere at 37° C. in DMEM and D-MEM/F-12 (1:1 mixture) medium (Invitrogen, Grand Island, N.Y.) with 10% fetal calf serum (Invitrogen, Grand Island, N.Y.), 100 U/mL penicillin (Invitrogen, Grand Island, N.Y.), 100 U/mL streptomycin (Invitrogen, Grand Island, N.Y.), 1 mg/mL G418 (Invitrogen, Grand Island N.Y.) and 0.2 mg/mL Hygromycin B (Invitrogen, Carlsbad, Calif.). Experimental cultures were grown overnight as a monolayer in 384-well tissue culture plates (0.06 ml/well-7500 cells/well). Each well was washed once with 0.1 mL of Krebs buffer. To each well was added 50 uL of Krebs buffer containing 100 uM phosphodiesterase inhibitor Ro20-1724 (Roche), 100 nM NECA (Sigma-Aldrich, St. Louis, Mo.), 0.02% BSA Fraction V (Roche Biochemicals), the test compound (appropriate concentration). The final concentration of DMSO was 1.1%. After incubation for 30-45 min, the wells were emptied and blotted on paper towel to remove residual solution. The HitHunter™ cAMP Assay Kit from DiscoverX for adherent cells (Fremont, Calif.) was used for lysing the cells and measuring cAMP concentrations. The compounds of Examples 1-20 exhibit $IC_{50}$ values of <5 μM.

What is claimed:
1. A compound of the formula

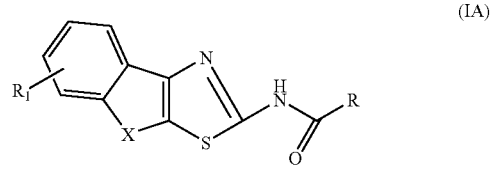

(IA)

or a pharmaceutically acceptable salt thereof, wherein
X is —$CH_2$—, —$CH_2CH_2$—, —$(CH_2)_3$— and O($CH_2$)—;
R is a 5- or 6- membered saturated or unsaturated carbocyclic or heterocyclic ring which optionally may contain one or more hetero atoms and said rings being optionally substituted with one or more substituents selected from the group consisting of halogen, lower alkyl, acetamidomethyl, alkoxycarbonyl amidomethyl, a nitrile group, a sulfonamido group, alkylsulfonyl, alkoxy, benzyl, benzoyl, arylsulfonyl and acyl which benzyl, benzoyl or arylsulfonyl is optionally substituted by halogen, trihalo lower alkyl, lower alkyl, alkoxy, alkylsulfonyl or cyano; and R₁ is selected from the group consisting of hydrogen, halogen, lower alkyl, alkoxy or a nitrile group.

2. The compound of claim 1 having the formula (IA)

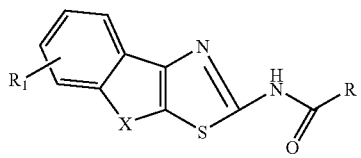

or a pharmaceutically acceptable salt thereof, wherein
X is —CH₂—, —CH₂CH₂—, —(CH₂)₃— and O(CH₂)—;
R is a 5- or 6- membered saturated or unsaturated carbocyclic or heterocyclic ring which optionally may contain one or more hetero atoms and said rings being optionally substituted with one or more substituents selected from the group consisting of halogen, lower-alkyl, a nitrile group, alkylsulfonyl, alkoxy and acyl.

3. The compound of claim 2 wherein X is —CH₂—.
4. The compound of claim 3 wherein R₁ is hydrogen, halogen or lower-alkoxy.
5. A compound of the formula

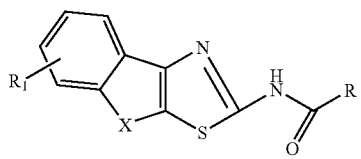

or the pharmaceutically acceptable salts thereof
  wherein R is phenyl or a heterocyclic ring selected from the group consisting of thienyl, pyridinyl, pyrazolyl, imidazolyl, furyl or piperidinyl, which phenyl or heterocyclic ring is optionally substituted with 1 to 3 substituents selected from the group consisting of halogen, hydroxy, nitrile, lower-alkyl, sulfonamido, lower-alkyl-sulfonyl, lower-alkoxy-carbonyl, lower-alkoxy-C(O)—NH—CH₂—, benzyl which is optionally substituted with CF₃, benzoyl which is optionally substituted with CF₃, or phenylsulfonyl
which is optionally substituted with CF₃
X is —CH₂—, —CH₂CH₂CH₂—, —(CH₂)₃— and O(CH₂)—; and
R₁ is selected from the group consisting of hydrogen, halogen, lower alkyl, alkoxy or a nitrile group.

6. A compound of claim 1 selected from the group consisting of
N-(8H-Indeno[1,2-d]thiazol-2-yl)-benzamide;
4-Fluoro-N-(8H-indeno[1,2-d]thiazol-2-yl)-benzamide;
4-Cyano-N-(8H-indeno[1,2-d]thiazol-2-yl)-benzamide;
N-(8H-indeno[1,2-d]thiazol-2-yl)-4-methyl-benzamide;
Thiophene-2-carboxylic acid (8H-indeno[1,2-d]thiazol-2-yl)-amide;
N-(8H-indeno[1,2-d]thiazol-2-yl)nicotinamide;
N-(8H-indeno[1,2-d]thiazol-2-yl)isonicotinamide;
2-Methyl-2H-pyrazole-3-carboxylic acid (8H-indeno[1,2-d]thiazol-2-yl)-amide;
N-(6-chloro-8H-indeno[1,2-d]thiazol-2-yl)-isonicotinamide;
1H-Pyrazole-4-carboxylic acid (8H-indeno[1,2-d]thiazol-2-yl)-amide;
N-(4,5-Dihydro-naphtho[1,2-d]thiazol-2-yl)-isonicotinamide;
N-(5,6-Dihydro-4H-3-thia-1-aza-benzo[e]azulen-2-yl)-isonicotinamide;
N-(4H-Chromeno[4,3-d]thiazol-2-yl)-isonicotinamide;
N-Naphtho[1,2-d]thiazol-2-yl-isonicotinamide and
3-Methyl-3H-imidazole-4-carboxylic acid (8H-indeno[1,2-d]thiazol-2-yl)-amide trifluoroacetate.

7. A compound of claim 1 selected from the group consisting of
4-(8H-Indenol[1,2-d]thiazol-2-ylcarbamoyl)-piperidine-1-carboxylic acid tert-butyl ester;
3-(trifluoromethyl-benzoyl)-piperidine-4-carboxylic acid (8H-indeno[1,2-d]thiazol-2-yl)-amide;
1-(3-trifluoromethyl-benzyl)-piperidine-4-carboxylic acid (9H-indeno[1,2-d]thiazol-2-yl)-amide;
1-(3-Trifluoromethyl-benzenesulfonyl)-piperidine-4-carboxylic acid (8H-indeno[1,2-d]thiazol-2-yl-amide;
N-(8H-Indeno[1,2-d]thiazol-2-yl) 3-fluorobenzamide;
N-(8H-Indeno[1,2-d]thiazol-2-yl) 3-hydroxybenzamide;
N-(8H-Indeno[1,2-d]thiazol-2-yl) 2-methylpent-5-enoylamide;
N-(8H-Indeno[1,2-d]thiazol-2-yl) 2-methylbutanoylamide;
N-(8H-Indeno[1,2-d]thiazol-2-yl) 5-methylsulfonylthiophene-2-carboxyamide;
N-(8H-Indeno[1,2-d]thiazol-2-yl) 2-furoylamide and
N-(6-Fluoro-8H-Indeno[1,2-d]thiazol-2-yl) 4-hydroxynicotinamide.

8. A compound of claim 1 selected from the group consisting of
N-(6-Fluoro-8H-Indeno[1,2-d]thiazol-2-yl) (4-aminosulfonyl)benzamide;
N-(6-Fluoro-8H-Indeno[1,2-d]thiazol-2-yl) (4-t-butoxycarbonylmethyl)benzamide;
N-(6-Fluoro-8H-Indeno[1,2-d]thiazol-2-yl) thiophene-3-carboxyamide;
N-(4,5-Dihydro-naphtho[1,2-d]thiazol-2-yl) 4-hydroxynicotinamide;
N-(4,5-Dihydro-naphtho[1,2-d]thiazol-2-yl) thiophene-3-carboxyamide;
N-(4,5-Dihydro-7-methoxynaphtho[1,2-d]thiazol-2-yl) 4-hydroxynicotinamide;
N-(4,5-Dihydro-7-methoxynaphtho[1,2-d]thiazol-2-yl) 5-methylsulfonylthiophene-2-carboxyamide;
N-(5,6-Dihydro-4H-3-thia-1-aza-benzo[e]azulen-2-yl) 4-hydroxynicotinamide;
N-(5,6-Dihydro-4H-3-thia-1-aza-benzo[e]azulen-2-yl) thiophene-3-carboxyamide;
N-(8H-Indeno[1,2-d]thiazol-2-yl) 3-chloro-4-hydroxybenzamide and
N-(8H-Indeno[1,2-d]thiazol-2-yl) (4-aminosulfonyl)benzamide.

9. A pharmaceutical composition comprising a compound of the formula

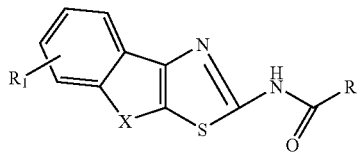

or a pharmaceutically acceptable salt thereof, wherein
X is —CH$_2$—, —CH$_2$CH$_2$—, —(CH$_2$)$_3$— and O(CH$_2$)—
R is a 5- or 6-membered saturated or unsaturated carbocyclic or heterocyclic ring which optionally may contain one or more hetero atoms and said rings being optionally substituted with one or more substituents selected from the group consisting of halogen, hydroxy, lower alkyl, acetamidomethyl, alkoxycarbonyl amidomethyl, a nitrile group, a sulfonamido group, alkylsulfonyl, alkoxy, benzyl, benzoyl, arylsulfonyl and acyl which benzyl, benzoyl, or arylsulfonyl is optionally substituted by halogen, trihalo lower alkyl, lower alkyl, alkoxy, alkylsulfonyl or cyano; and R$_1$ is selected from the group consisting of hydrogen, halogen, lower alkyl, alkoxy or a nitrile group together with a pharmaceutically acceptable excipient.

* * * * *

UNITED STATES PATENT AND TRADEMARK OFFICE
CERTIFICATE OF CORRECTION

PATENT NO. : 7,407,977 B2
APPLICATION NO. : 11/193766
DATED : August 5, 2008
INVENTOR(S) : Jianping Cai and Adrian Wai-Hing Cheung et al.

It is certified that error appears in the above-identified patent and that said Letters Patent is hereby corrected as shown below:

On the Title Page item (75) Inventors: please delete "Adrian Wai-Hing" and
Insert --Adrian Wai-Hing Cheung--

Signed and Sealed this

Twenty-third Day of February, 2010

David J. Kappos
*Director of the United States Patent and Trademark Office*

UNITED STATES PATENT AND TRADEMARK OFFICE
CERTIFICATE OF CORRECTION

PATENT NO. : 7,407,977 B2 Page 1 of 1
APPLICATION NO. : 11/193766
DATED : August 5, 2008
INVENTOR(S) : Jianping Cai, et al.

It is certified that error appears in the above-identified patent and that said Letters Patent is hereby corrected as shown below:

In Claim 5 at Column 23, Line 51, please delete "–$CH_2$-, -$CH_2$-$CH_2CH_2$-, -$(CH_2)_3$- and $O(CH_2)$-; and"

Insert -- –$CH_2$-, -$CH_2CH_2$-, -$(CH_2)_3$- and $O(CH_2)$-; and --

Signed and Sealed this

Twenty-second Day of June, 2010

David J. Kappos
*Director of the United States Patent and Trademark Office*